United States Patent [19]

Farge et al.

[11] 4,261,999
[45] Apr. 14, 1981

[54] THIAZOLOTHIENOPYRIDINES AND ANTI-VIRAL COMPOSITIONS THEREOF

[75] Inventors: Daniel Farge, Thiais; Alain Jossin, St. Cloud; Gerard Ponsinet, Sucy-en-Brie; Daniel Reisdorf, Thiais, all of France

[73] Assignee: Rhone-Poulenc Industries, Paris, France

[21] Appl. No.: 100,523

[22] Filed: Dec. 5, 1979

[30] Foreign Application Priority Data

Dec. 7, 1978 [FR] France .................. 78 34483
Oct. 29, 1979 [FR] France .................. 79 26732

[51] Int. Cl.$^3$ .................. A61K 31/47; C07D 513/14
[52] U.S. Cl. .................. 424/258; 424/263; 546/80; 546/114; 546/143; 546/305
[58] Field of Search .................. 546/80; 424/258, 263

[56] References Cited

U.S. PATENT DOCUMENTS

| | | | |
|---|---|---|---|
| 3,979,397 | 9/1976 | Harsanyi et al. | 546/80 |
| 4,064,247 | 12/1977 | Farge et al. | 546/80 X |
| 4,153,698 | 5/1979 | Farge et al. | 546/80 X |

FOREIGN PATENT DOCUMENTS 2378030 8/1978 France .
166699 1/1965 U.S.S.R. .................. 546/80

*Primary Examiner*—Richard A. Schwartz
*Attorney, Agent, or Firm*—Stevens, Davis, Miller & Mosher

[57] ABSTRACT

Thienopyridine derivatives of the formula:

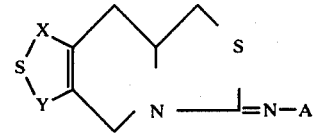

wherein the symbol A represents pyrid-3-yl, isoquinol-5-yl, or a 3-alkylisoquinol-5-yl group in which the alkyl radical is of 1 through 10 carbon atoms, and one of the symbols X and Y represents a single bond and the other represents the vinylene radical, are new compounds possessing useful pharmacological properties. They are particularly useful as anti-viral agents and, in certain cases, as analgesics, anti-inflammatory agents and antipyretics.

9 Claims, No Drawings

THIAZOLOTHIENOPYRIDINES AND ANTI-VIRAL COMPOSITIONS THEREOF

DESCRIPTION

This invention relates to new therapeutically useful thienopyridine derivatives, to processes for their preparation and pharmaceutical compositions containing them.

The thienopyridine derivatives of the present invention are those of general formula:

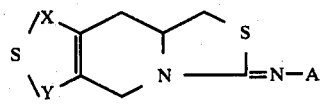

wherein the symbol A represents a pyrid-3-yl or isoquinol-5-yl radical or a 3-alkylisoquinol-5-yl radical in which the alkyl moiety contains 1 to 10 carbon atoms in a straight or branched chain, and one of the symbols X and Y represents a single bond and the other represents the vinylene radical (i.e. —CHαCH—), and acid addition salts thereof.

The compounds of general formula I can exist in (R) and (S) forms and the invention includes both such forms and mixtures thereof, preferably the (RS) form.

According to a feature of the present invention, the thienopyridine derivatives of general formula I are prepared by the process which comprises the cyclisation of a 4,5,6,7-tetrahydrothienopyridine derivative of the general formula:

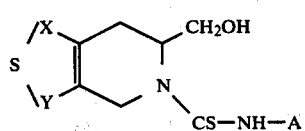

wherein A, X and Y are as hereinbefore defined. The cyclisation is generally carried out by heating a compound of general formula II in an acid medium. It is particularly advantageous to carry out the reaction at a temperature between 65° C. and the reflux temperature of the reaction mixture in an aqueous solution of an inorganic acid, for example in hydrochloric acid, preferably 4N to 8N.

The 4,5,6,7-tetrahydrothienopyridines of general formula II can be obtained by the reaction of an isothiocyanate of the general formula:

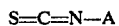

(wherein A is as hereinbefore defined) with a hydroxymethyl-4,5,6,7-tetrahydrothienopyridine of the general formula:

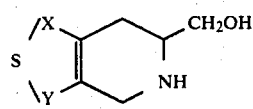

wherein X and Y are as hereinbefore defined. The reaction is generally carried out in an organic solvent such as an alcohol, e.g. ethanol, at a temperature between 0° and 50° C.

The compounds of general formula IV can be prepared by reducing a carboxy-4,5,6,7-tetrahydrothienopyridine of the general formula:

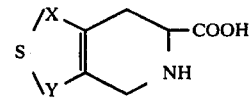

wherein X and Y are as hereinbefore defined. The reduction is generally carried out by means of lithium aluminium hydride in an organic solvent, such as tetrahydrofuran, at a temperature between 20° C. and the reflux temperature of the reaction mixture.

The carboxy-4,5,6,7-tetrahydrothienopyridines of general formula V can be prepared from thien-2-yl (or thien-3-yl)-alanine in accordance with the method described in Belgian Pat. No. 862,695 or U.S. Pat. No. 4,147,787.

When using a thienylalanine in the L form, the product of general formula I is obtained in the (S) form.

When using a thienylalanine in the D form, the product of general formula I is obtained in the (R) form.

When using a thienylalanine in the DL form, the product of general formula I is obtained in the (RS) form.

The isothiocyanates of general formula III can be prepared according to Belgian Pat. Nos. 844,927 and 863,083, British Pat. No. 150,3091 or U.S. Pat. No. 4,153,698.

According to another feature of the invention, the thienopyridine derivatives of general formula I are prepared by the process which comprises reacting an amine of the general formula:

A—NH$_2$

VI (wherein A is as hereinbefore defined) with a salt of the general formula:

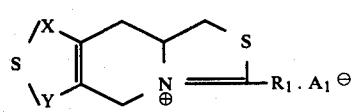

wherein X and Y are as hereinbefore defined, R$_1$ represents a chlorine atom or an alkylthio radical containing 1 to 4 carbon atoms (preferably methylthio) or the benzylthio radical, and A$_1$$^\ominus$ represents an anion, such as a chloride, iodide, sulphate, tetrafluoroborate or fluorosulphonate ion. When R$_1$ represents a chlorine atom, A$_1$$^\ominus$ represents a chloride ion. When R$_1$ represents an alkylthio or benzylthio radical, A$_1$$^\ominus$ represents an iodide, sulphate, tetrafluoroborate or fluorosulphonate ion.

When R$_1$ represents a chlorine atom and A$_1$$^\ominus$ represents a chloride ion, the reaction is preferably carried out in an organic solvent, such as acetonitrile, in the presence of a base, such as triethylamine, at a temperature between 15° and 50° C.

When R$_1$ represents an alkylthio or benzylthio radical and A$_1$$^\ominus$ represents an iodide, sulphate, tetrafluoroborate or fluorosulphate ion, the reaction is preferably carried out in a basic organic solvent, such as pyridine, at a temperature between 15° and 50° C.

The salts of general formula VII wherein R$_1$ represents a chlorine atom and A$_1$$^\ominus$ represents a chloride ion can be obtained by the reacting of a chlorinating agent, such as phosgene, phosphorus pentachloride, thionyl chloride or oxalyl chloride, with a thiazolo-thienopyridinethione of the general formula:

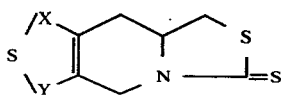 VIII wherein X and Y are as hereinbefore defined. The reaction is generally carried out in an organic solvent or in a mixture of organic solvents, such as a mixture of toluene and tetrahydrofuran, at a temperature between 0° and 70° C.

The salts of general formula VII wherein $R_1$ represents an alkylthio or benzylthio radical and $A_1^\ominus$ represents an iodide, sulphate, tetrafluoroborate or fluorosulphonate ion can be obtained, respectively, by the action of a reactive ester of the general formula:

$$R_2-A_2 \qquad \text{IX}$$

(wherein $R_2$ represents an alkyl radical containing 1 to 4 carbon atoms, or the benzyl radical, and $A_2$ represents an iodine atom or an alkoxysulphonyloxy radical), or by the action of triethyloxonium tetrafluoroborate, or methyl fluorosulphonate, on a compound of general formula VIII. The reaction is generally carried out in the presence or absence of an organic solvent, such as methylene chloride, at a temperature of about 20° C.

The thiazolothienopyridine derivatives of general formula VIII can be obtained by reacting carbon disulphide, in a basic medium, with a 4,5,6,7-tetrahydrothienopyridine of the general formula:

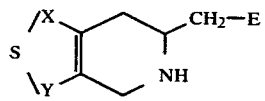 X wherein X and Y have corresponding meanings, and E represents a halogen atom or a hydroxysulphonyloxy radical. The reaction is generally carried out in an aqueous medium, in the presence of sodium hydroxide, at a temperature of about 20° C.

The compound of general formula X can be obtained by reacting an inorganic acid with a hydroxymethyl-4,5,6,7-tetrahydrothienopyridine of general formula IV wherein X and Y have corresponding meanings.

When it is desired to obtain a compound of general formula X wherein E represents a hydroxysulphonyloxy radical, the reaction is generally carried out using sulphuric acid in an aqueous medium at a temperature of about 100° C., or in an organic solvent (such as dimethylformamide), in the presence of N,N'-dicyclohexylcarbodiimide at a temperature of about 20° C.

When it is desired to obtain a compound of general formula X wherein E represents a bromine atom, the reaction is generally carried out using a 48% aqueous solution of hydrobromic acid at the reflux temperature of the reaction mixture, and the product is isolated in the form of the hydrobromide.

When it is desired to obtain a compound of general formula X wherein E represents a chlorine atom, the reaction is generally carried out using thionyl chloride in an organic solvent, such as chloroform saturated with hydrogen chloride, at the reflux temperature of the reaction mixture, and the resulting product is then isolated in the form of the hydrochloride.

The thienopyridine derivatives of general formula I may be converted by known methods into acid addition salts. (By the term "known methods" is meant methods heretofore used or described in the chemical literature). The acid addition salts may be obtained by reacting the thienopyridine derivatives with acids in appropriate solvents. As organic solvents there may be used alcohols, ketones, ethers or chlorinated hydrocarbons. The salt which is formed is precipitated, if necessary after concentration of the solution, and is isolated by filtration or decantation.

The thienopyridine derivatives of general formula I and/or their acid addition salts can optionally be purified by physical methods such as crystallisation or chromatography.

The thienopyridine derivatives of general formula I and their pharmaceutically acceptable acid addition salts possess useful pharmacological properties. They are anti-viral agents and some of them are also particularly valuable as analgesic, anti-pyretic or anti-inflammatory agents.

The anti-viral activity is particularly effective against viruses of the rhinovirus group. On cell cultures of human MRC-5 fibroblasts, infected with human type 1 B rhinovirus (R 1112 strain), the compounds of general formula I cause complete inhibition of the cytopathogenic effect and of the multiplication of the viruses, at concentrations of between 7 to 60 μg/cc (maximum non-cytotoxic concentration) and 0.7 to 7 μg/cc (minimum inhibitory concentration), which corresponds to a chemotherapeutic index of between 1 and 40.

The anti-inflammatory activity manifests itself in rats at doses of between 20 and 100 mg/kg animal body weight, administered orally, in accordance with the technique of K. F. Benitz and L. M. Hall, Arch, Int. Pharmacodyn., 144, 185 (1963).

The analgesic activity manifests itself in rats at doses of between 5 and 50 mg/kg animal body weight, administered orally, in the technique of E. Siegmund et al., Proc. Soc. Exp. Biol. Med., 95, 729 (1957), and at doses of between 2.5 and 50 mg/kg animal body weight, administered orally, in the technique of L. O. Randall and J. J. Selitto, Arch. Int. Pharmacodyn., 111, 409 (1957), modified by K. F. Swingle et al., Proc. Soc. Exp. Biol. Med., 137, 536 (1971).

The anti-pyretic activity manifests itself in rats at doses of between 2.5 and 50 mg/kg animal body weight, administered orally, in the technique of J. J. Loux et al., Toxicol. Appl. Pharmacol., 22, 674 (1972).

Furthermore, the acute toxicity to mice of the thienopyridine derivatives of the invention is more than 900 mg/kg animal body weight, administered orally.

Of particular interest are those compounds of general formula I wherein the symbol A represents a pyrid-3-yl, isoquinol-5-yl or 3-methylisoquinol-5-yl radical, and especially the (RS) form of such compounds.

Amongst these compounds, those which are more especially active as anti-rhinoviral agents conform to the general formula:

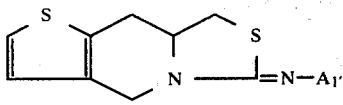

XI wherein A₁, represents a pyrid-3-yl, isoquinol-5-yl or 3-methylisoquinol-5-yl radical, and very particularly 6-[(pyrid-3-yl)imino]-4,8,8a,9-tetrahydrothiazolo[3,4-a]thieno[2,3-d]pyridine and 6-[(3-methylisoquinol-5-yl)imino]-4,8,8a,9-tetrahydrothiazolo[3,4-a]thieno[2,3-d]pyridine.

The compounds which are more especially active in terms of their analgesic and anti-pyretic activity are those of general formula I wherein A represents a pyrid-3-yl or 3-methylisoquinol-5-yl radical, and very particularly 6-[(3-methylisoquinol-5-yl)imino]-4,8,8a,9-tetrahydrothiazolo[3,4-a]thieno[2,3-d]-pyridine and 7-[(3-methylisoquinol-5-yl)imino]-4,4-a,5,9-tetrahydrothiazolo[3,4-a]thieno[3,2-d]pyridine.

For therapeutic purposes the thienopyridine derivatives of general formula I are employed as such or in the form of pharmaceutically acceptable salts, i.e. salts containing anions which are relatively innocuous to the animal organism in therapeutic doses of the salts (such as hydrochlorides, sulphates, nitrates, phosphates, acetates, propionates, succinates, benzoates, fumarates, maleates, tartrates, theophyllinacetates, salicylates, phenolphthalinates and methylene-bis-β-hydroxynaphthoates) so that the beneficial physiological properties inherent in the bases are not vitiated by side-effects ascribable to the anions.

The following Examples illustrate the preparation of the new thienopyridine derivatives of the present invention.

EXAMPLE 1

A suspension of (RS)-6-hydroxymethyl-5-[(pyrid-3-yl)thiocarbamoyl]-4,5,6,7-tetrahydrothieno[3,2-c]pyridine (2.3 g) in 6 N hydrochloric acid (34 cc) is heated under reflux for 2 hours. The resulting brown solution is decolorised with animal charcoal and filtered. The filtrate is rendered alkaline to pH 11 with a 15% aqueous solution of potassium carbonate and extracted with methylene chloride (150 cc and then 3×100 cc). The organic extracts are combined and dried over sodium sulphate. After filtering and concentrating the filtrate to dryness under reduced pressure (25 mmHg; 3.3 kPa) at 40° C., an oil is obtained which crystallises slowly. This oil is dissolved in a mixture, heated under reflux, of isopropanol and diisopropyl ether (4:1 by volume; 100 cc). The solution is cooled and kept at +5° C. for 20 hours. The resulting solid is filtered off, washed with diisopropyl ether (50 cc) and dried under reduced pressure (0.1 mm Hg; 0.013 kPa) at 60° C. (RS)-6-[(Pyrid-3-yl)imino]-4,8,8a,9-tetrahydrothiazolo[3,4-a]thieno[2,3-d]pyridine (1.3 g) is thus obtained in the form of white crystals melting at 145° C.

(RS)-6-Hydroxymethyl-5-[(pyrid-3-yl)thiocarbamoyl]-4,5,6,7-tetrahydrothieno[3,2-c]pyridine can be prepared in the following manner:

A solution of 3-isothiocyanatopyridine (1.36 g) in absolute ethanol (40 cc) is added dropwise, at a temperature of about 0° C., to a solution of (RS)-6-hydroxymethyl-4,5,6,7-tetrahydrothieno[3,2-c]pyridine (1.69 g) in absolute ethanol (60 cc). The resulting solution is stirred for 20 hours at a temperature of about 20° C. and the solid formed is then filtered off. The filtrate is evaporated to dryness under reduced pressure (25 mm Hg; 3.3 kPa) at 40° C. and a white solid is obtained which is combined with the solid isolated by filtration. These solids are dissolved in a mixture, heated under reflux, of isopropanol and diisopropyl ether (1:2 by volume; 130 cc) and the solution, after cooling, is kept at +5° C. for 20 hours. The resulting crystals are filtered off, washed with diisopropyl ether (50 cc) and dried at 20° C. under reduced pressure (0.1 mm Hg; 0.013 kPa). (RS)-6-Hydroxymethyl-5-[(pyrid-3-yl)thiocarbamoyl]-4,5,6,7-tetrahydrothieno[3,2-c]pyridine (2.3 g) is thus obtained in the form of white crystals melting at 186° C.

3-Isothiocyanatopyridine can be prepared in accordance with the method described in Belgian Pat. No. 844,927 or British Pat. No. 1,503,091.

(RS)-6-Hydroxymethyl-4,5,6,7-tetrahydrothieno[3,2-c]pyridine can be prepared in the following manner:

(RS)-6-Carboxy-4,5,6,7-tetrahydrothieno[3,2-c]pyridine (3.7 g) is added, under a nitrogen atmosphere and in small portions, to a solution of lithium aluminum hydride (1.1 g) in tetrahydrofuran (45 cc); the resulting suspension is heated under reflux for 4 hours. After cooling, water (1.35 cc), 5N aqueous sodium hydroxide solution (0.95 cc) and water (4.35 cc) are successively added dropwise. The inorganic salts formed are filtered off and washed with methylene chloride (5×20 cc). The filtrates are combined and evaporated to dryness under reduced pressure (25 mm Hg; 3.3 kPa) at 60° C. The residue is dissolved in boiling acetonitrile (15 cc) and the solution is cooled and then kept at 5° C. for 20 hours. The resulting crystals are filtered off, washed with cyclohexane and dried at 20° C. under reduced pressure (0.1 mm Hg; 0.013 kPa). (RS)-6-Hydroxymethyl-4,5,6,7-tetrahydrothieno[3,2-c]pyridine (1.2 g), melting at 110° C., is thus obtained.

(RS)-6-Carboxy-4,5,6,7-tetrahydrothieno[3,2-c]pyridine can be prepared in accordance with the method described in Belgian Patent 862695 or U.S. Pat. No. 4,147,787.

EXAMPLE 2

A suspension of (RS)-5-hydroxymethyl-6-[(pyrid-3-yl)thiocarbamoyl]-4,5,6,7-tetrahydrothieno[2,3-c]pyridine (2.3 g) in 6 N hydrochloric acid (34 cc) is heated under reflux for 2 hours. The resulting brown solution is decolorised with animal charcoal and filtered. The filtrate is rendered alkaline to pH 11 with a 15% aqueous solution of potassium carbonate and extracted with methylene chloride (150 cc and then 3×100 cc). The organic extracts are combined and dried over sodium sulphate. After filtering and concentrating the filtrate to dryness under reduced pressure (25 mm Hg; 3.3 kPa) at 40° C., an oil is obtained which crystallises slowly. This oil is dissolved in a mixture, heated under reflux, of isopropanol and diisopropyl ether (4:1 by volume; 100 cc). The solution is cooled at +5° C. for 20 hours. The solid is filtered off, washed with diisopropyl ether (50 cc) and dried at 60° C. under reduced pressure (0.1 mm Hg; 0.013 kPa). (RS)-7-[(Pyrid-3-yl)imino]-4,4a,5,9-tetrahydrothiazolo[3,4-a]thieno[3,2-d]pyridine (1.2 g) is obtained in the form of white crystals melting at 136° C.

(RS)-5-Hydroxymethyl-6-[(pyrid-3-yl)-thiocarbamoyl]-4,5,6,7-tetrahydrothieno[2,3-c]pyridine can be prepared in the following manner:

A solution of 3-isothiocyanatopyridine (1.36 g) in absolute ethanol (40 cc) is added dropwise, at a temperature of about 0° C., to a solution of (RS)-5-hydroxymethyl-4,5,6,7-tetrahydrothieno[2,3-c]pyridine (1.69 g) in absolute ethanol (60 cc). The resulting solution is stirred for 20 hours at a temperature of about 20° C. and the solid formed is then filtered off. The filtrate is evaporated to dryness under reduced pressure (25 mm Hg; 3.3 kPa) at 40° C. and a white solid is obtained which is combined with the solid isolated by filtration. These solids are dissolved in a mixture, heated under reflux, of isopropanol and diisopropyl ether (1:2 by volume; 150 cc) and the solution, after cooling, is kept at +5° C. for 20 hours. The resulting crystals are filtered off, washed with diisopropyl ether (50 cc) and dried at 20° C. under reduced pressure (0.1 mm Hg; 0.013 kPa). (RS)-5-Hydroxymethyl-6-[(pyrid-3-yl)thiocarbamoyl]-4,5,6,7-tetrahydrothieno[2,3-c]pyridine (2.3 g) is thus obtained in the form of white crystals melting at 165° C.

(RS)-5-Hydroxymethyl-4,5,6,7-tetrahydrothieno[2,3-c]pyridine can be prepared in the following manner:

(RS)-5-Carboxy-4,5,6,7-tetrahydrothieno[2,3-c]pyridine hydrochloride (98.5 g) is added, at about 20° C., in small portions and under an argon temperature to a suspension of lithium aluminum hydride (25.6 g) in tetrahydrofuran (3000 cc). The suspension is then heated under reflux for 6 hours. After cooling in an ice-bath, water (30 cc), a 0.6 N aqueous sodium hydroxide solution (22.5 cc) and water (87 cc) are successively added. The insoluble material is filtered off and then washed with methylene chloride (5×400 cc). The filtrate and the washings are combined and dried over sodium sulphate. After filtration and evaporation to dryness under reduced pressure (30 mm Hg; 4 kPa) at 50° C., a pale yellow solid is obtained.

This solid is dissolved in a mixture of diisopropyl ether and ethanol (1:1 by volume; 200 cc) and the solution is decolorised with charcoal and filtered. The filtrate is cooled in an ice-bath and the resulting crystals are filtered off. After washing with diisopropyl ether and then drying under reduced pressure (0.5 mm Hg; 0.07 kPa) at 50° C., (RS)-5-hydroxymethyl-4,5,6,7-tetrahydrothieno[2,3-c]pyridine (31.4 g) is isolated in the form of very pale yellow crystals melting at 157°–158° C.

(RS)-5-Carboxy-4,5,6,7-tetrahydrothieno[2,3-c]pyridine hydrochloride can be prepared according to Belgian Pat. No. 862,695 or U.S. Pat. No. 4,147,787.

EXAMPLE 3

A suspension of (RS)-6-hydroxymethyl-5-[(isoquinol-5-yl)thiocarbamoyl]-4,5,6,7-tetrahydrothieno[3,2-c]pyridine (6.7 g) in 6 N hydrochloric acid (70 cc) is heated to 100° C. This temperature is maintained for 30 minutes. The resulting brown solution is cooled and then rendered alkaline to pH 10 with 10 N aqueous sodium hydroxide solution and extracted with methylene chloride (3×250 cc). The organic extracts are combined, washed with water (3×150 cc) and then dried over sodium sulphate. After filtration and concentration under reduced pressure (25 mm Hg; 3.3 kPa) at 40° C., a brown residue (8 g) is obtained which is purified by chromatography on silica (200 g) contained in a column of diameter 3.5 cm, elution being carried out with a mixture of methylene chloride and methanol (99:1 by volume; 500 cc) and then with a mixture of methylene chloride and methanol (98:2 by volume; 500 cc) and 125 cc fractions being collected.

Fractions 11 to 22 are combined and concentrated to dryness under reduced pressure (25 mm Hg; 3.3 kPa) at 40° C. The residue is crystallised from acetonitrile (300 cc) to give (RS)-6-[(isoquinol-5-yl)imino]-4,8,8a,9-tetrahydrothiazolo[3,4-a]thieno[2,3-d]pyridine (4.7 g) melting at 198° C.

(RS)-6-Hydroxymethyl-5-[(isoquinol-5-yl)-thiocarbamoyl]-4,5,6,7-tetrahydrothieno[3,2-c]pyridine can be prepared in the following manner:

5-Isothiocyanatoisoquinoline (5.1 g) is added to a solution of (RS)-6-hydroxymethyl-4,5,6,7-tetrahydrothieno[3,2-c]pyridine (4.3 g) in absolute ethanol (55 cc). After 48 hours at a temperature of about 20° C., the resulting crystals are filtered off, washed with diisopropyl ether (75 cc) and then dried at 40° C. under reduced pressure (0.1 mm Hg; 0.013 kPa). (RS)-6-Hydroxymethyl-5-[(isoquinol-5-yl)thiocarbamoyl]-4,5,6,7-tetrahydrothieno[3,2-c]pyridine (6.7 g), melting at 185° C., is thus obtained.

5-Isothiocyanatoisoquinoline can be prepared in accordance with the method described in Belgian Pat. No. 844 927 or British Pat. No. 1 503 091.

EXAMPLE 4

A suspension of (RS)-5-hydroxymethyl-6-[(isoquinol-5-yl)thiocarbamoyl]-4,5,6,7-tetrahydrothieno[2,3-c]pyridine (21 g) in 6 N hydrochloric acid (220 cc) is heated under reflux for 1.5 hours. The resulting brown solution is cooled, decolorised with animal charcoal and filtered. The filtrate is rendered alkaline to pH 11 with a 15% aqueous solution of potassium carbonate and extracted with methylene chloride (300 cc and then 3×200 cc). The organic extracts are combined and dried over sodium sulphate. After filtering and concentrating the filtrate to dryness under reduced pressure (25 mm Hg; 3.3 kPa) at 40° C., a pale yellow solid is obtained. This solid is dissolved in boiling isopropanol (800 cc); the resulting solution is cooled to +5° C. and kept at that temperature for 20 hours. The solid formed is filtered off and taken up in boiling isopropanol (500 cc); the resulting solution is cooled to +5° C. and kept at that temperature for 20 hours. The solid formed is filtered off, washed with diisopropyl ether (2×50 cc) and dried at 60° C. under reduced pressure (0.1 mm Hg; 0.013 kPa). (RS)-7-[(Isoquinol-5-yl)imino]-4,4a,5,9-tetrahydrothiazolo[3,4-a]thieno[3,2-d]pyridine (13.9 g) is thus obtained in the form of pale yellow crystals melting at 171° C.

(RS)-5-Hydroxymethyl-6-[(isoquinol-5-yl)thiocarbamoyl]-4,5,6,7-tetrahydrothieno[2,3-c]pyridine can be prepared in the following manner:

A solution of 5-isothiocyanatoisoquinoline (1.2 g) in absolute ethanol (32.5 cc) is added dropwise, at a temperature of about 0° C., to a solution of (RS)-5-hydroxymethyl-4,5,6,7-tetrahydrothieno[2,3-c]pyridine (1.0 g) in absolute ethanol (7.5 cc). After 20 hours at a temperature of about 20° C., the resulting white crystals are filtered off, washed with diisopropyl ether (50 cc) and then dried under reduced pressure (0.1 mm Hg; 0.013 kPa) at 20° C. A solid (2.1 g) is obtained which is dissolved in a mixture, heated under reflux, of ethanol and diisopropyl ether (1:9 by volume; 30 cc). The solution is cooled and kept at +5° C. for 20 hours and the resulting solid is then filtered off and dried at 60° C. under reduced pressure (0.1 mm Hg; 0.013 kPa) to give (RS)-5-hydroxymethyl-6-[(isoquinol-5-yl)thiocarbamoyl]-4,5,6,7-tetrahydrothieno[2,3-c]pyridine (1.7 g) in the form of white crystals melting at 145° C. with decomposition.

EXAMPLE 5

A suspension of (RS)-6-hydroxymethyl-5-[(3-methylisoquinol-5-yl)thiocarbamoyl]-4,5,6,7-tetrahydrothieno[3,2-c]pyridine (6.8 g) in 6 N hydrochloric acid (70 cc) is heated to 100° C.; this temperature is maintained for 30 minutes. The resulting brown solution is cooled and then rendered alkaline to pH 10 with 10 N aqueous sodium hydroxide solution and extracted with methylene chloride (3×150 cc). The organic extracts are combined, washed with water (3×150 cc) and then dried over sodium sulphate. After filtering and concentrating the filtrate to dryness under reduced pressure (25 mm Hg; 3.3 kPa) at 40° C., a brown residue (7.3 g) is obtained which is purified by chromatography on silica (200 g) contained in a column of diameter 3.5 cm, elution being carried out with a mixture of methylene chloride and methanol (49:1 by volume; 500 cc) and then with a mixture of methylene chloride and methanol (48:2 by volume; 500 cc) and 125 cc fractions being collected.

Fractions 2 to 5 are combined and concentrated to dryness under reduced pressure (25 mm Hg) at 40° C. The residue is dissolved in boiling isopropanol (100 cc); the solution is cooled and then kept at 5° C. for 20 hours. The resulting crystals are filtered off, washed with isopropanol (3×15 cc) and dried at 60° C. under reduced pressure (0.1 mm Hg; 0.013 kPa). (RS)-6-[(3-Methylisoquinol-5-yl)imino]-4,8,8a,9-tetrahydrothiazolo[3,4-a]thieno[2,3-d]pyridine (4.1 g), melting at 159° C., is thus obtained.

(RS)-6-Hydroxymethyl-5-[(3-methylisoquinol-5-yl)thiocarbamoyl]-4,5,6,7-tetrahydrothieno[3,2-c]pyridine can be prepared in the following manner:

5-Isothiocyanato-3-methylisoquinoline (5.1 g) is added to a solution of (RS)-6-hydroxymethyl-4,5,6,7-tetrahydrothieno[3,2-c]pyridine (3.4 g) in absolute ethanol (55 cc). After 15 hours at a temperature of about 20° C., the resulting crystals are filtered off, washed with diisopropyl ether and then dried at 60° C. under reduced pressure (0.1 mm Hg; 0.013 kPa). (RS)-6-Hydroxymethyl-5-[(3-methylisoquinol-5-yl)thiocarbamoyl]-4,5,6,7-tetrahydrothieno[3,2-c]pyridine (6.9 g), melting at 190° C., is thus obtained.

5-Isothiocyanato-3-methylisoquinoline can be prepared in accordance with the method described in Belgian Pat. No. 863 083 or U.S. Pat. No. 4,153,698.

EXAMPLE 6

A suspension of (RS)-5-hydroxymethyl-6-[(3-methylisoquinol-5-yl)thiocarbamoyl]-4,5,6,7-tetrahydrothieno[2,3-c]pyridine (17 g) in 6 N hydrochloric acid (170 cc) is heated under reflux for 2 hours. The compound gradually passes into solution. The resulting pale yellow solution is cooled in an ice-bath and then rendered alkaline to pH 12 with a 15% aqueous solution of potassium carbonate and extracted with methylene chloride (500 cc and then 3×200 cc). The organic extracts are combined, washed with water (100 cc) and then dried over sodium sulphate. After filtering and concentrating the filtrate to dryness under reduced pressure (30 mm Hg; 4 kPa) at 40° C., a faintly coloured oil is obtained which crystallises slowly.

This oil is dissolved in boiling isopropanol (250 cc) and the solution is then cooled and kept at about 5° C. for 20 hours. The resulting crystals are filtered off, washed with isopropanol and then dried at 50° C. under reduced pressure (0.5 mm Hg; 0.07 kPa). (RS)-7-[(3-Methylisoquinol-5-yl)imino]-4,4a,5,9-tetrahydrothiazolo[3,4-a]thieno[3,2-d]pyridine (12 g) is obtained in the form of white crystals melting at 159° C.

(RS)-5-Hydroxymethyl-6-[(3-methylisoquinol-5-yl)thiocarbamoyl]-4,5,6,7-tetrahydrothieno[2,3-c]pyridine can be prepared in the following manner:

A solution of 5-isothiocyanato-3-methylisoquinoline (10 g) in absolute ethanol (200 cc) is added dropwise, at a temperature of about 0° C., to a solution of (RS)-5-hydroxymethyl-4,5,6,7-tetrahydrothieno[2,3-c]pyridine (8.45 g) in absolute ethanol (200 cc). After stirring for ten minutes at 0° C., a copious white precipitate is formed.

The mixture is stirred for 20 hours at 20° C. and the resulting solid is then filtered off. The crystals are washed with diisopropyl ether and then dried at 40° C. under reduced pressure (0.5 mm Hg; 0.07 kPa) to give (RS)-5-hydroxymethyl-6-[(3-methylisoquinol-5-yl)thiocarbamoyl]-4,5,6,7-tetrahydrothieno[2,3-c]pyridine (17 g) melting at 145° C. with decomposition.

The present invention includes within its scope pharmaceutical compositions which comprise, as active ingredient, at least one of the compounds of general formula I, or a pharmaceutically acceptable acid addition salt thereof, in association with a pharmaceutically acceptable carrier or adjuvant. The invention includes especially such preparations made up for intranasal, oral, parenteral, rectal or topical administration.

Solid compositions for oral administration include tablets, pills, powders (especially in gelatin capsules), and granules. In such solid compositions the active compound is admixed with at lest one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water or liquid paraffin. Besides inert diluents such compositions may also comprise adjuvants, such as wetting, emulsifying and suspending agents, and sweetening, flavouring and aromatizing agents. The compositions according to the invention, for oral administration also include capsules of absorbable material such as gelatin containing the active substance with or without the addition of diluents or excipients.

Preparations according to the invention for intranasal or parenteral administration include sterile aqueous or non-aqueous solutions, suspensions or emulsions. Examples of non-aqueous solvents or vehicles are propylene glycol, polyethylene glycol, vegetable oils (in particular olive oil, sweet-almond oil or coconut oil) and injectable organic esters such as ethyl oleate. These compositions may also contain adjuvants such as preserving, wetting, emulsifying and dispersing agents (e.g. soya lecithin). They may be sterilized, for example, by incorporation in the compositions of sterilising agents, by irradiation, by heating or by addition of a preservative. They may also be manufactured in the form of sterile solid compositions, which can be dissolved in a sterile injectable medium immediately before use.

Compositions for rectal administration are suppositories which contain, in addition to the active substance, excipients such as cacao butter or a suitable wax base.

Compositions for topical administration may be in the form of ointments.

The percentage of active ingredient in the compositions of the invention may be varied, it being necessary that it should constitute a proportion such that a suitable dosage shall be obtained. The compositions are particularly useful in human therapy by virtue of their anti-viral action and, if appropriate, their anti-inflammatory, analgesic or anti-pyretic action. They are indicated, in particular, for the treatment of viral infections of the respiratory tract and, if appropriate, for the treatment of inflammatory diseases (ankylotic spondylarthritis, acute articular rheumatism and arthrosis), acute and chronic pain, rheumatic and traumatic algias, dental, neurological and visceral pain, various algias (pain experienced by cancer patients) and febrile conditions.

In human therapy, the doses of the thienopyridine derivative(s) depend on the desired effect and the duration of the treatment. For an adult, they are generally between 100 and 2000 mg per day, administered orally. They can reach 100 mg per day when administered nasally (drops or sprays).

In general, the physician will decide the posology considered appropriate, taking into account the age, weight and other factors peculiar to the patient being treated.

The following Examples illustrate pharmaceutical compositions according to the invention.

EXAMPLE 7

Tablets containing a 100 mg dose of active product and having the following composition are prepared in accordance with the usual technique:

| | |
|---|---|
| (RS)-6-[(3-methylisoquinol-5-yl)imino]-4,8,8a,9-tetrahydrothiazolo[3,4-a]thieno-[2,3-d]pyridine | 0.100 g |
| starch | 0.110 g |
| precipitated silica | 0.035 g |
| magnesium stearate | 0.005 g |

EXAMPLE 8

Tablets containing a 100 mg dose of active product and having the following composition are prepared in accordance with the usual technique:

| | |
|---|---|
| (RS)-6-[(pyrid-3-yl)imino]-4,8,8a,9-tetrahydrothiazolo[3,4-a]thieno-[2,3-d]pyridine | 0.100 g |
| starch | 0.110 g |
| precipitated silica | 0.035 g |
| magnesium stearate | 0.005 g |

EXAMPLE 9

A 1% oily solution for intranasal administration is prepared by dissolving (RS)-6-[(3-methylisoquinol-5-yl)imino]-4,8,8a,9-tetrahydrothiazolo[3,4-a]thieno[2,3-d]pyridine (1 g) in olive oil (100 cc) at 40°–50° C. and filtering the resulting solution on a Millipore filter. For use, the solution is applied to the nasal mucous membrane with the aid of a dropper.

We claim:

1. A thienopyridine derivative of the formula:

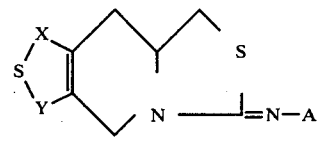

wherein the symbol A represents pyrid-3-yl, isoquinol-5-yl, or 3-methylisoquinol-5-yl and one of the symbols X and Y represents a single bond and the other represents the vinylene radical, or a pharmaceutically acceptable acid addition salt thereof.

2. A thienopyridine derivative according to claim 1 which is 6-[(pyrid-3-yl)imino]-4,8,8a,9-tetrahydrothiazolo[3,4-a]thieno[2,3-d]pyridine or a pharmaceutically acceptable acid addition salt thereof.

3. A thienopyridine derivative according to claim 1 which is 7-[(pyrid-3-yl)imino]-4,4a,5,9-tetrahydrothiazolo[3,4-a]thieno[3,2-d]pyridine or a pharmaceutically acceptable acid addition salt thereof.

4. A thienopyridine derivative according to claim 1 which is 6-[(isoquinol-5-yl)imino]-4,8,8a,9-tetrahydrothiazolo[3,4-a]thieno[2,3-d]pyridine or a pharmaceutically acceptable acid addition salt thereof.

5. A thienopyridine derivative according to claim 1 which is 7-[(isoquinol-5-yl)imino]-4,4a,5,9-tetrahydrothiazolo[3,4-a]thieno[3,2-d]pyridine or a pharmaceutically acceptable acid addition salt thereof.

6. A thienopyridine derivative according to claim 1 which is 6-[(3-methylisoquinol-5-yl)imino]-4,8,8a,9-tetrahydrothiazolo[3,4-a]thieno[2,3-d]pyridine or a pharmaceutically acceptable acid addition salt thereof.

7. A thienopyridine derivative according to claim 1 which is 7-[(3-methylisoquinol-5-yl)imino]-4,4a,5,9-tetrahydrothiazolo[3,4-a]thieno[3,2-d]pyridine or a pharmaceutically acceptable acid addition salt thereof.

8. A thienopyridine derivative according to claim 1 which is in the (RS) form.

9. A pharmaceutical composition suitable for use as an anti-viral agent which comprises a therapeutically effective amount of a thienopyridine derivative as claimed in claim 1, or a pharmaceutically acceptable acid addition salt thereof, in association with a compatible pharmaceutically acceptable carrier.

* * * * *